US009351791B2

(12) United States Patent
Schoenbach et al.

(10) Patent No.: US 9,351,791 B2
(45) Date of Patent: May 31, 2016

(54) SYSTEM AND METHODS OF TREATMENT USING ELECTROMAGNETIC ILLUMINATION (75) Inventors: Karl H. Schoenbach, Norfolk, VA (US); Shu Xiao, Norfolk, VA (US)

(73) Assignee: OLD DOMINION UNIVERSITY RESEARCH FOUNDATION, Norfolk, VA (US)

( * ) Notice: Subject to any disclaimer, the term of this patent is extended or adjusted under 35 U.S.C. 154(b) by 1145 days.

(21) Appl. No.: 13/145,220

(22) PCT Filed: Jan. 20, 2010

(86) PCT No.: PCT/US2010/021533
§ 371 (c)(1),
(2), (4) Date: Oct. 28, 2011

(87) PCT Pub. No.: WO2010/085501
PCT Pub. Date: Jul. 29, 2010

(65) Prior Publication Data
US 2012/0035511 A1 Feb. 9, 2012

Related U.S. Application Data (60) Provisional application No. 61/145,936, filed on Jan. 20, 2009.

(51) Int. Cl.
*A61B 18/18* (2006.01)
*A61N 7/02* (2006.01)
(52) U.S. Cl.
CPC ............. *A61B 18/18* (2013.01); *A61B 18/1815* (2013.01); *A61N 7/02* (2013.01)
(58) Field of Classification Search
CPC ............... A61B 18/18; A61B 18/1815; A61B 18/1206; A61B 2018/2085; A61B 2018/00767; A61B 2018/00648; A61B 2018/00613; A61B 2018/00761; A61B 2018/00452; A61B 2018/00577; A61N 7/02
USPC ............. 606/32–35, 41, 45–50; 607/101, 102, 607/154, 156
See application file for complete search history.

(56) References Cited

U.S. PATENT DOCUMENTS

| 4,669,475 A | 6/1987 | Turner |
| 5,500,012 A * | 3/1996 | Brucker et al. ............... 607/122 |
| 6,261,831 B1 * | 7/2001 | Agee .......................... 435/285.2 |
| 6,821,274 B2 * | 11/2004 | McHale et al. ................. 606/41 |
| 2002/0010491 A1 | 1/2002 | Schoenbach et al. |
| 2003/0069619 A1 | 4/2003 | Fenn et al. |

(Continued)

FOREIGN PATENT DOCUMENTS

WO    WO 2007/024734    * 3/2007

OTHER PUBLICATIONS

International Search Report and Written Opinion issued in Application No. PCT/US2010/021533 dated Mar. 19, 2010 (9 pages).

*Primary Examiner* — Michael Peffley
(74) *Attorney, Agent, or Firm* — Polsinelli PC (57) ABSTRACT A method of inducing local cell death in patient tissue is provided. The method includes generating first and second radiation, conveying the radiation to a focusing element, and focusing the radiation on a target with the focusing element. A system for inducing local cell death in patient tissue is also provided. The system includes a power source for generating narrow-band and/or ultra-wideband radiation, and a focusing element for focusing the radiation on a target.

27 Claims, 9 Drawing Sheets

(56) References Cited

U.S. PATENT DOCUMENTS

| | | |
|---|---|---|
| 2003/0088180 A1 | 5/2003 | Van Veen et al. |
| 2005/0240239 A1 | 10/2005 | Boveja et al. |
| 2006/0217703 A1* | 9/2006 | Chornenky et al. ............. 606/41 |
| 2007/0016274 A1 | 1/2007 | Boveja et al. |
| 2008/0065059 A1* | 3/2008 | Lukowiak et al. ............. 606/33 |
| 2008/0160090 A1 | 7/2008 | Oraevsky et al. |
| 2008/0208052 A1 | 8/2008 | Lepivert et al. |
| 2008/0252293 A1 | 10/2008 | Lagae et al. |
| 2008/0262295 A1 | 10/2008 | Kendale |
| 2009/0125091 A1* | 5/2009 | Schoenbach et al. ......... 607/156 |
| 2010/0286573 A1* | 11/2010 | Schoenbach ..................... 601/3 |
| 2011/0112520 A1* | 5/2011 | Michael ......................... 606/13 |

\* cited by examiner

SYSTEM AND METHODS OF TREATMENT USING ELECTROMAGNETIC ILLUMINATION

FIELD OF THE INVENTION

The subject matter described herein is related to the field of patient treatments, and more particularly, to techniques for treating patients through cell inducing death by heating tissue.

BACKGROUND OF THE INVENTION

Heating of tissue to temperatures which cause cell death can be used as a form of cancer treatment. Heating to moderately increased temperatures (on the order of 42 to 45 C.), known as hyperthermia, has been used, for example, to damage or kill cancer cells and to make cancer cells more sensitive to collateral modes of treatment. Increasing the temperature to at least 50 C. for extended exposure (minutes) causes coagulation necrosis, a method known as ablation. Different forms of energy can be used to induce cell death, including microwaves, radio waves, and ultrasound.

In treating tumors or other cancers, an optimum effect can be achieved if the tumor is locally heated such that healthy tissue remains unaffected. The treatment can be effected through external approaches, such as that undertaken for treating skin cancer. An external approach to treating skin cancer, for example, utilizes microwaves with slight tissue penetration depth to induce cell death in melanoma tumors.

For treating deeper lying tumors, heat sources can be inserted directly into a tumor to induce cell death or cause ablation. A procedure known as radio frequency ablation (RFA) utilizes radio frequency radiation, which is applied to the tumor. Radio frequency also has been used to treat deeper lying tumors and cancerous tissues, but typically only for regional hyperthermia. According to this technique, large volumes of tissue are usually heated by placing external applications around that portion of a patient's body that is to be treated.

Conventionally, if local heating of a tumor or part of a tumor is to be undertaken, short-wavelength radiation can be used, the tissue penetration depth being relatively slight. An antenna can be used to transfer the energy from the source to the tumor. Because of the small penetration depth, this technique can be effective for skin cancers, but typically cannot be used to effectively treat deeper lying tissue. Alternatively, for deeper penetration, an interstitial technique can be used, according to which a probe is inserted into the tumor in order to induce cell death by transfer of energy from the tip of the probe to the tumor.

SUMMARY

The subject matter described herein is directed to systems and methods for locally inducing cell death in patient tissue using ultra-wideband radiation. In one aspect, local cell death is induced by generating ultra-wideband radiation and focusing the radiation using high-power focusing emitters. In another aspect, local cell death is induced by generating ultra-wideband radiation and focusing the radiation using certain types of lenses.

In one exemplary embodiment, narrowband radiation can be applied to a target region and ultra-wideband radiation can be applied to the target region.

Described herein is a system for locally inducing cell death in patient tissue. The system includes a power source for generating first and second radiation and a focusing element for focusing the first and second radiation on a target in which the first radiation elevates the temperature of the target. As an example, the focusing element can be a prolate spheroidal reflector or a lens.

As another example, the first radiation can be narrowband radiation in the microwave range, and the frequency of the narrowband radiation can be at least 100 MHz. Additionally, the frequency of the narrowband radiation can be less than 100 GHz. The first radiation can be delivered in the form of a pulse, and the pulse duration of the first radiation can be less than ten seconds. In another arrangement, the pulse duration of the first radiation can be longer than one microsecond. The power level of the first radiation can also exceed approximately 100 watts, and the power level of the first radiation can be less than 1 megawatt.

The second radiation can be ultra-wideband radiation using an ultra-short electrical pulse, which can have a rise time of less than one nanosecond. The ultra-short electrical pulse can have a pulse duration of more than 10 picoseconds and a pulse duration of less than 10 nanoseconds. The ultra-short electrical pulse can have a power level of at least one megawatt and a power level of less than one gigawatt.

Also described herein is a method for inducing cell death in patient tissue. The method can include the steps of generating first and second radiation, conveying the first and second radiation to a focusing element and focusing the first and second radiation on a target with the focusing element. The first radiation can elevate the temperature of the target, and the second radiation affects cell functions by electrical means. As an example, the focusing element can be at least one prolate spheroidal reflector or at least one focusing lens.

In one arrangement, the second radiation can be ultra-wideband radiation, and the ultra-wideband radiation can be an ultra-short electrical pulse. As an example, the ultra-short electrical pulse can have a rise time of less than one nanosecond.

Also described herein is a method of treating biological tissue. The method can include the steps of focusing narrowband radiation on the biological tissue to elevate a temperature of the tissue, focusing ultra-wideband radiation on the biological tissue to modify cell functions and subsequently treating the tissue with another mode of treatment. In one arrangement, the narrowband radiation can be a microwave pulse, and the microwave pulse can induce a temperature increase in the tissue ranging from 1 to 50 C.

In another arrangement, the other mode of treatment can be ionizing radiation or the local application of a chemotherapeutic agent. Also, the other mode of treatment can include the local application of drugs which lead to cell death or can include ultrasound radiation.

The step of focusing can include focusing the ultra-wideband radiation with at least one prolate spheroidal reflector or with at least one focusing lens. In addition, the ultra-wideband radiation can be an ultra-short electrical pulse.

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

The subject matter described herein is directed to systems and methods for treating a patient using ultra-wideband radiation. By utilizing ultra-wideband radiation, it is possible to induce local heating with external sources, not only on the surface of the patient's body, but in deeper lying tissue as well. Priority is claimed from U.S. Ser. No. 61/145,936, which is incorporated by reference herein in its entirety.

Figure 1:
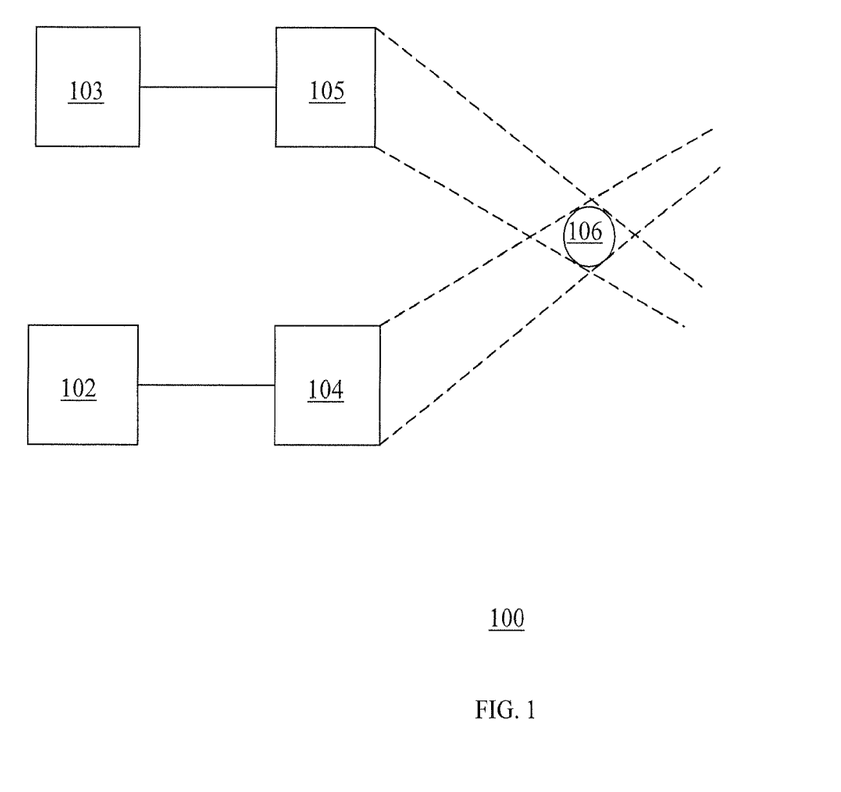
FIG. 1 is a schematic diagram of a system for generating local cell death in tissue.

Referring initially to FIG. 1, a system 100, according to one embodiment, is schematically illustrated. The system 100 illustratively includes an energy source 102 for generating a first radiation, such as a narrowband radiation, including radiowaves, microwaves, soundwaves, and combinations thereof. Narrowband radiation can be defined as single frequency radiation having a pulse duration of approximately one second (or even higher) down to approximately $10^{-6}$ seconds, depending on the power level. The system 100 further illustratively includes a focusing element 104 for focusing the radiation generated by the energy source 102 on a target 106. The target 106, more particularly, can be a tumor or some other diseased tissue identified in the body of patient (human or animal). As explained below, however, in alternative uses, the system 100 can be used for other purposes, including treating a subject for corrective or cosmetic reasons. A second energy source 103 can be utilized for generating a second radiation, such as ultra-wideband radiation, which can be applied to the target 106 using a second focusing element 105. Ultra-wideband radiation can be defined as radiation emitted from an antenna in the form of ultra-short electrical pulses having a pulse duration of less than approximately ten nanoseconds but greater than approximately 10 picoseconds. While system 100 utilizes separate radiation sources and focusing elements for applying different radiation to the target, the present disclosure contemplates using any number of components. For instance, a single radiation source and focusing element can be utilized to apply multiple radiation types to the target, such as in alternating applications. The particular number and types of radiation can also vary, including more than two, which may include both narrowband and ultra-wideband radiation.

In one embodiment, the focusing element 104 and/or 105 can comprise one or more prolate spheroidal reflectors for focusing the radiation generated by the energy source 102 and/or 103. In another embodiment, the focusing element 104 and/or 105 can comprise a lens for focusing the radiation on the target 106. The present disclosure also contemplates combinations of reflectors and/or lenses being utilized to apply the radiation to the target region 106.

Irradiation time for cell death using RF or microwave radiations may depend on pulse duration. For example, cell death can be obtained with an exposure time of 0.1 hours (six minutes) by increasing the local body temperature to about 50 C. Decreasing the exposure time to one second, however, requires that the local body temperature be elevated to 57 C. to cause cell death. Reaching temperatures on that order of magnitude in seconds and less is possible with high power microwaves. If the microwave power is increased—but at a decreased exposure time such that the total deposited energy is less than that used to generate cell death—we can expect both electrical effects (due to the high power level) and thermal effects.

Operatively, the system 100 can generate narrowband radiation for raising the temperature of the target 106 to a desired temperature and can also generate ultra-short electrical pulses. By using ultra-short electrical pulses, with rise times on the order of less than 1 nanosecond, for example, it is possible to focus the energy into a small volume with characteristic dimensions of millimeters. Since the frequency distribution for the electromagnetic waves that correlate to such ultra-short pulses—even for 100 ps pulses—reaches only to a few GHz, the penetration depth of the radiation exceeds that of millimeter wave radiation. Indeed, the penetration depth obtained using ultra-short pulses can considerably exceed that obtained with millimeter wave radiation. It is, therefore, possible to reach tumors located more deeply in a patient's body with this external approach, rather than using probes that must be inserted into the patient.

Figure 2:
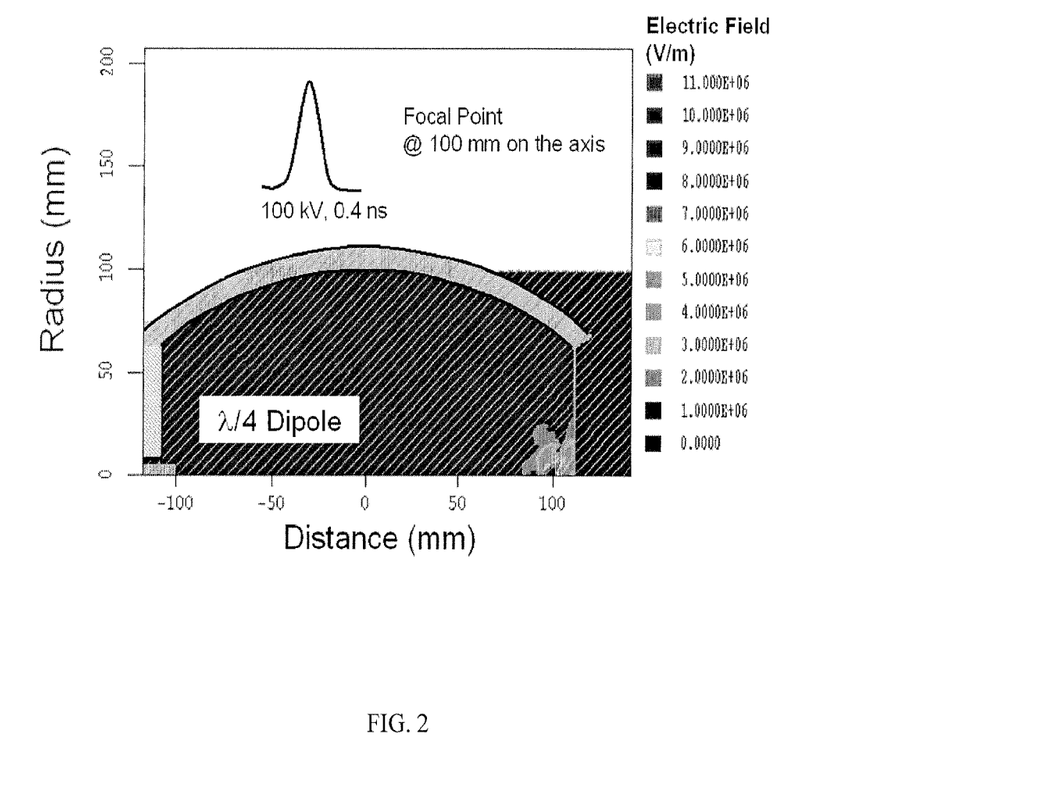
FIG. 2 is a plot of the electric field distribution that can be obtained using the system of FIG. 1.

FIG. 2 provides a plot showing this effect. In particular, FIG. 2 shows the computed electric field distribution indicating the large values of electric field in the focal volume at a 100 mm distance. The focusing effect can be achieved, according to one embodiment, if the focusing element 104 comprises an oblate spheroidal reflector and/or lenses, which focuses the energy emitted from an antenna in the left focal volume to that in the right focal volume.

The energy distribution, which corresponds to the temperature distribution, can scale with the square of the electric field intensity. Correspondingly, the volume where critical temperatures are reached is even smaller than that characterized by the electric field value. It is known that tumor tissue generally has a higher conductivity than healthy tissue. Thus, the effect of the electromagnetic field in the tumor is even more amplified. The energy can be focused into a well defined volume, if ultra-short pulses are used.

As will be understood by one of ordinary skill in the art, localized hyperthermia can cause apoptosis of tumor cells. This connection of hyperthermia with apoptosis has been demonstrated in several studies. Mild hyperthermia also has been shown to increase the sensitivity of tumors to other agents. Accordingly, a combination therapy, where local heating is combined with another procedure (e.g., ionizing radiation therapy or local administration of toxins, such as cisplatinum or bleomycin) may increase the probability for inducing cell death.

The use of hyperthermia, generated locally by means of the exemplary system 100, or a similar ultra-wideband imaging system, is not restricted to the elimination of tumor cells. Other unwanted tissue, such as adipose tissue, can also be affected by hyperthermia. Focusing the ultra-wideband radiation into fat tissue is likely to cause apoptosis of fat cells. Since through the focusing effect, the energy density at the skin would be minimized, this treatment can affect only non-wanted tissue, without adversely affecting a patient's skin.

Figure 3:
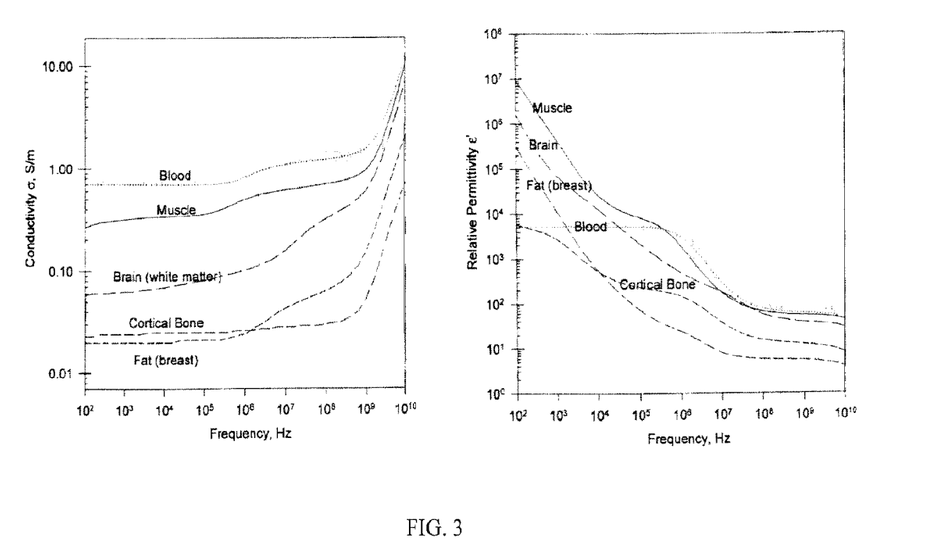
FIG. 3 is a plot of conductivity and permittivity versus frequency for various tissues.

Referring to FIG. 3, conductivity and permittivity for various tissues are shown. The electrical bandwidth, f, (frequency where the signal falls to one over square root of two of its maximum value) of a Gaussian pulse with pulse width, w, is given as: $f=1/7.56 w$, for a pulse width of 100 ps, f is approximately 1.3 GHz. The penetration or skin depth, respectively, is given as: $\delta=1/\sqrt{2\pi f\sigma\mu}$, where f is the frequency of the electromagnetic radiation, $\sigma$ is the conductivity of the tissue, and $\mu$ is its permeability. The absolute permeability is $4\pi10^{-7}$ Vs/Am. For fat and bone tissue as shown in FIG. 3, the conductivity at 1.3 GHz is on the order of or less than 0.1 A/Vm. Correspondingly, the absorption depth for electromagnetic radiation of this frequency is approximately 3 cm. This is the distance over which the signal decays to 1/e (=0.37) of its value at the surface. In muscle tissue, with its higher conductivity, the absorption depth can be less. It becomes possible to reach deeper lying tumors (distances of several cm from skin) with this external approach, rather than using intrusive probes into the body.

Localized hyperthermia causes apoptosis of tumor cells. Mild hyperthermia increases the sensitivity of tumors to other agents. A combination therapy, where local heating combined with another procedure (such as using the effect of high electric fields of nanosecond pulses itself or ionizing radiation therapy or toxins such as cisplatinum or bleomycin, locally administered) can increase the probability for tumor reduction.

The use of hyperthermia, such as generated locally by means of an ultrawide-band imaging system, is not restricted to the elimination of tumor cells. Other unwanted tissue, such as adipose tissue, may also be affected by hyperthermia. Focusing the ultrawide-band radiation into fat tissue can cause apoptosis of fat cells. Since, through the focusing effect, the energy density at the skin would be minimized, this treatment promises to affect the unwanted tissue more than the skin.

EXAMPLE

A calculation of the temperature obtainable with an ultra-wide-band focusing system is shown in the following. Based on modeling results similar to those shown in FIG. 1, the electric field in the focal volume can reach values of more than 100 kV/cm. With a pulse duration of 100 ps, the energy density in the focal point (assuming a resistivity of the tissue of 50 Ohm cm) is 0.1 Joule per cubic centimeter, assuming that that the focal volume is approximately 0.2 $cm^3$ (corresponding to a sphere with diameter of 0.37 cm). This corresponds to a temperature increase of approximately 0.025 degree K per pulse. Using a pulse power system that generates the required electric fields at a repetition rate of 1 kHz, the local temperature increase in the tissue after a 1-second exposure would be 25 degrees K. Even with thermal loss processes, such as thermal conduction, which would cause a reduction in the peak energy, the temperature locally would exceed that required for apoptosis induction.

This increase in local temperature coupled with the effects of high electric field pulses is expected to enhance the probability for a synergistic effect leading to a loss of viability of the tumor cells either through apoptosis or other effects. The possibility to use ultrawideband radiation at extreme power levels opens a new method of radiation therapy using nonionizing radiation. The possibility to focus the energy into small volumes allows us to obtain high temperature locally, where it is needed, with only minor effects on neighboring tissue.

The systems used for cell death can be a single antenna or an antenna array with multiple antennas. The focusing element in the antenna can be a prolate spheroid reflector, a lens or a combination of both. Each antenna can be capable of delivering electric pulses with amplitudes of hundreds of kilovolts at pulse widths less than 1 ns, which are produced by a subnanosecond pulsed power system and/or pulsed narrowband radiofrequency or microwave radiation. In addition, auxiliary heating by sound waves can be included to deposit more energy in the focal volume, allowing a local temperature rise, which can be controlled independently from the ultrawideband pulse and the narrow-band radiation. Using ultrawideband pulses in conjunction with heating through narrowband, pulsed, high power radiowaves or microwaves or soundwaves can also offer the possibility of obtaining synergistic effects. After heating the target with pulsed microwaves or sound waves (such as less than the diffusion time constant of the tissue), ultrawideband pulses can then be applied to create electric-field-induced but non-thermal effects, like apoptosis, platelet activation, calcium release, and other cell functions. These effects can be synergistic and means they could be stronger than those caused by ultrawideband pulses alone without extra heating.

Figure 4:
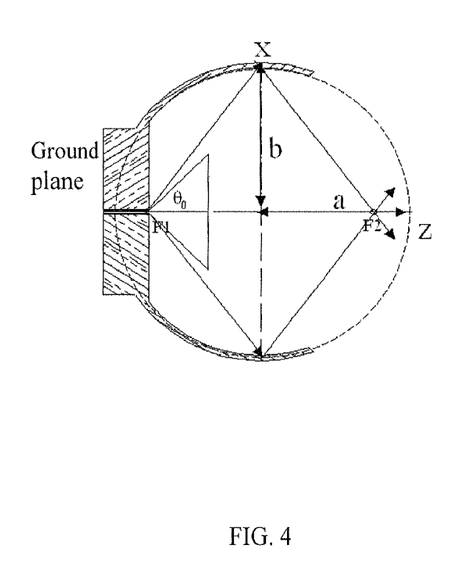
FIG. 4 is a high power impulse antenna according to one embodiment.

Referring to FIG. 4, an antenna system that could be used to radiate either or both of ultrawideband radiation or pulsed narrowband radiation is shown that comprises a conical wave launching system and a prolate spheroidal reflector. The wave launching system can have rotational symmetry about the z-axis. The apex of the cone can be at the first focal point F1. A wave emitted from F1 can be a spherical TEM wave with its source at F1. The apex can be connected to the inner conductor of a coaxial cable feed from one of the ends of the reflector. Such a conical wave launcher above a ground plane can be an unbalanced structure; thus, no balun is required to feed the wave launcher.

The launched wave can be reflected on the prolate spheroidal reflector surface to converge at the second focal point (F2). The electric field at F2 can comprise prepulse, impulse and postpulse. The prepulse, caused by the diffraction at the edge of the wave launcher cone can have the same polarity as the impulse, the scattered signal from the reflector. Due to rotational symmetry, the electric field at the second focal point can have only longitudinal components.

Figure 5:
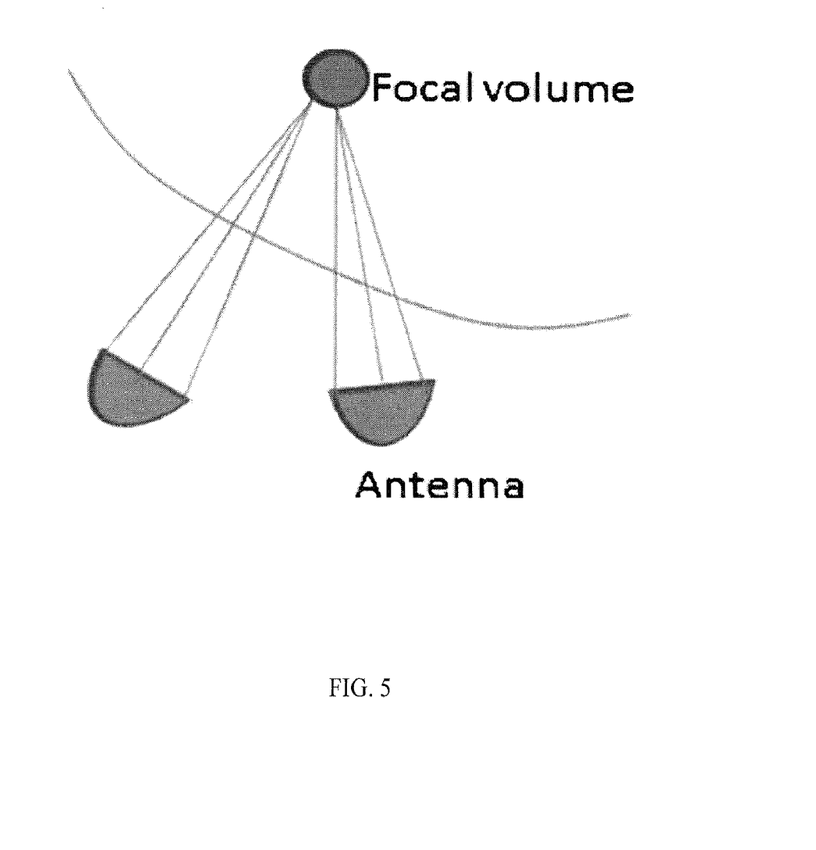
FIG. 5 is a multiple antennae system to increase power deposition in the focal volume according to one embodiment.
Figure 6:
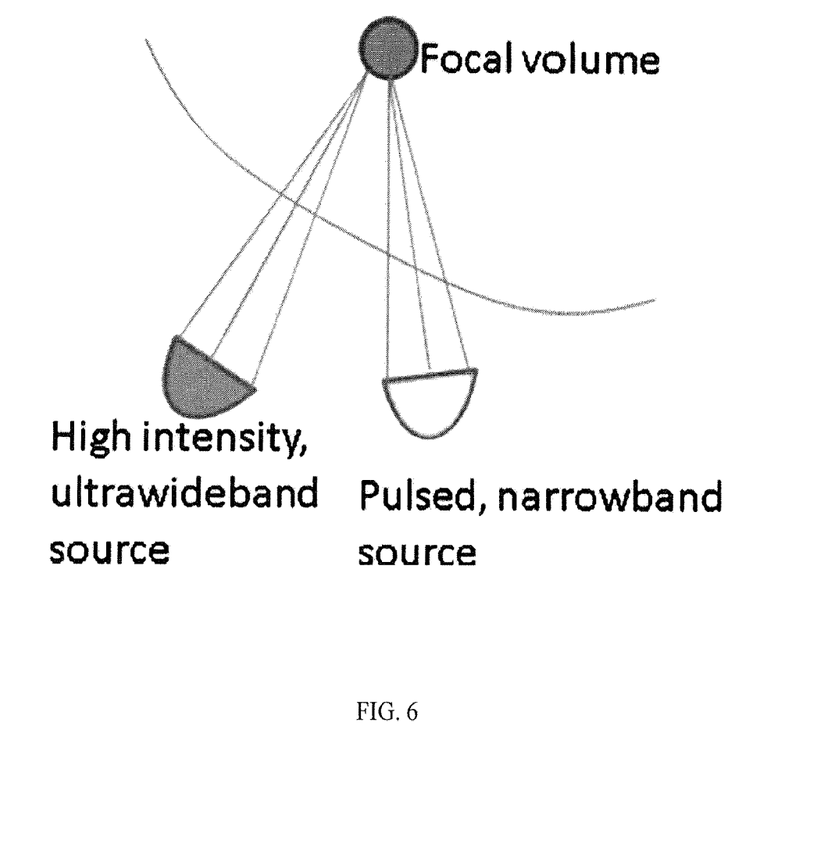
FIG. 6 is a multiple antennae system using narrowband waves according to one embodiment.

Referring to FIGS. 5 and 6, to increase the intensity of the electric power (ultrawideband radiation or pulsed narrowband radiation) in the focal volume, multiple antennas can be used, and these antennas can radiate from different angles. This can be realized by firing several antennas at the same time and/or firing each antenna alternately, which increases the total power deposition. Because the passage through normal tissues is spread over a larger volume, this approach will effectively lower the power deposition in the normal tissues.

To heat the target to temperatures that approach hyperthermia conditions, narrow-band, pulsed high power radiowaves or microwaves (the pulse width preferably less than the heat diffusion time constant of the tissue) can be used in addition to the pulsed, ultrawideband and high intensity electromagnetic pulses. The pulse width of the microwave radiation can be shorter than the characteristic time for thermal conduction or diffusion, to reach high temperatures in the focal volume. Ultrawideband pulses with high electric fields can be combined with the heating produced by narrow band pulses to create a synergistic effect and cause an increased rate of cell death. This can be achieved by introducing one or more separate antennas into the array for focusing narrow band waves into the target.

Figure 7:
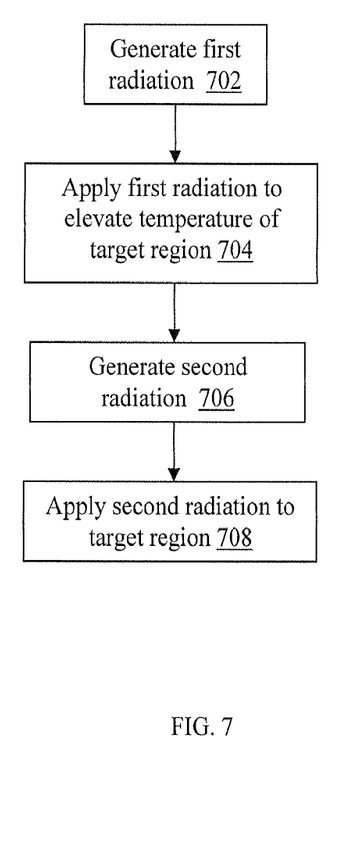
FIG. 7 is a flowchart of exemplary steps in a method for generating local hyperthermia in tissue, according another embodiment.

In one embodiment, a control system can be utilized for determining and applying the radiation, to the target region, such as narrow band radiation followed by ultra-wideband radiation. For instance, the narrowband radiation can be applied to the target region for approximately 1 ms to raise the temperature of the target region and then the ultra-wideband radiation can then be applied to achieve the desired cellular effect, such as apoptosis. The present disclosure contemplates various temperatures and time periods being utilized with the exemplary embodiments. The exemplary embodiments can also utilize various types of radiation or energy in addition to or in place of the narrowband or ultra-wideband radiation, including ionizing radiation, particle beams and so forth. The energy can be generated from a single source or from multiple sources and can be applied and/or focused using a single focusing device or a plurality of focusing devices. In one embodiment, the target is elevated to a temperature that facilitates application of the ultra-wideband radiation and achieving apoptosis FIG. 7 is a flowchart of exemplary steps of a method 700 for inducing local hyperthermia, according to another embodiment. The method 700 can include generating a first radiation at step 702, such as pulsed microwaves or soundwaves. At step 704, the first radiation is applied to the target region to elevate the temperature, such as through use of a focusing element. The temperature reached can depend on the tissue type. In step 706, a second radiation can be generated and applied to the target region in step 708, such as through use of another focusing element. The second radiation can be an ultra-wideband radiation. Application of the ultra-wideband radiation, such as through pulses, can achieve the desired cellular effect, such as apoptosis, platelet activation, calcium release and so forth.

In still another embodiment, however, treatment of a patient includes the inducement of local hyperthermia in conjunction with an additional therapy. The additional therapy, according to one embodiment comprises ionizing radiation therapy. In an alternative embodiment, the additional therapy comprises the local administration of a toxin. The toxin can be, for example, cisplatinum, bleomycin, or similar such toxin.

The temperature of the focal volume caused by heating with ultrawideband pulses can be such that the target leads by itself to changes in cell functions or cell death. It can also be increased by other means to such levels that the target in the focal volume becomes more sensitive to chemical toxins, ionizing radiations, or the effects of pulsed electric fields, so to achieve a synergistic effect. In the latter case, the effects of high electric field pulses may enhance the probability for a synergistic effect leading to a loss of viability of the tumor cells either through apoptosis or other effects.

To reach such thermal conditions, one can heat the target with lower-amplitude UWB pulses, acoustic waves or non-ionizing radiation (microwave), allowing a local temperature rise, which can be less than the diffusion time constant of the tissue. An example given here is heating with narrow-band microwave in conjunction with high-intensity ultrawideband pulses. After heating the target with pulsed microwaves, ultrawideband pulses are then applied to create electric-field-induced but non-thermal effects, such as apoptosis, platelet activation, calcium release, and other cell functions. These effects can be synergistic and means they could be stronger than those caused by ultrawideband pulses alone without extra heating.

Figure 8:
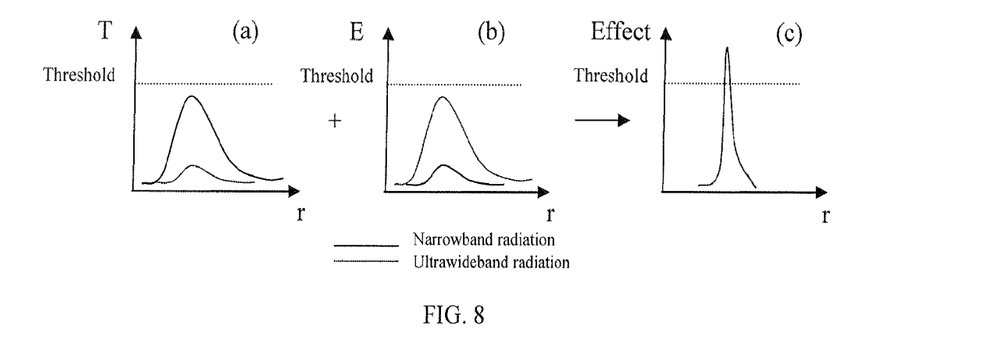
FIG. 8. Temperature and electric field distribution in the focal volume as a result of the heating by narrowband microwave and ultrawideband pulses, respectively: (a) The temperature due to narrowband microwave heating is dominant. (b) The electric field of ultrawideband pulses is dominant (c) A synergistic effect occurs due to the combination of two effects, shown in (a) and (b), resulting in a much higher spatial resolution.

Shown in FIG. 8 (a) is the temperature distribution in the focal volume. Narrowband microwave heats the target to a temperature close to the hyperthermia effect (shown as the curve with the higher amplitude), whereas the ultrawideband pulses does not cause a significant temperature rise (the curve with the lower amplitude). However, in FIG. 8(b), the electric field of ultrawideband pulses is much higher (the curve with the higher amplitude) than that of narrowband microwave radiation (the curve with the lower amplitude) and close to the level enough to cause electric-field-induced effect, such as apoptosis, so the overall effect of temperature rise and electric-field-induced effect can be enhanced as a result. Additional benefit of this concept is that the effective volume is confined to a much smaller volume (shown in FIG. 8 (c)) due to the overlap of the bell-shape curves (FIG. 8 (a) and FIG. 8 (b)), so the spatial resolution is improved.

Figure 9:
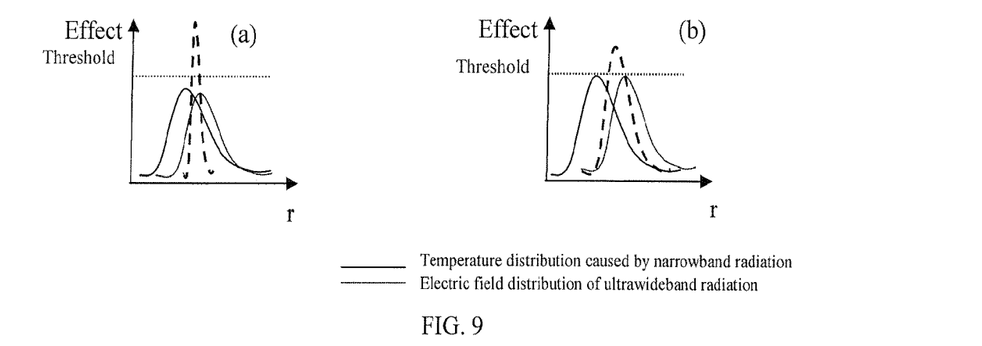
FIG. 9. Varying the relative position of the temperature peak and electric-field peak allows shifting the effective zone spatially. (a) The two peaks are close to each other, resulting in a reduced effective volume. (b) The two peaks can be separated by a certain distance, which allows scanning the target volume over a distance determined by the temperature and electric field distribution.

This concept also allows us to shift the effective volume in space. In FIGS. 9(a) and 9(b), the temperature distribution caused by narrowband microwave is shown in the solid curve to the left, and the solid curve to the right shows the electric-field distribution of ultrawideband pulses. Also in FIGS. 9(a) and 9(b), the effective volume is represented by the dashed curve. Even though the focal points of ultrawideband pulses and narrowband microwave are not identical, one could still achieve a synergistic effect due to the combination of these two effects by adjusting the relative position of the temperature peak and electric-field peak, which allows us to scan the target of an extended volume and reduces the constraint of having the temperature pulse and electric field pulse perfectly aligned in space.

One can apply the ultrawideband pulses at different times after the heating with pulsed narrowband microwave radiation. Because the temperature of the focal volume rises in a very short time (~ms) and decays over a much longer time, one can control the timing of the effect by setting the different delay time to apply the ultrawideband pulse (FIG. 10) and consequently control the intensity of the desired effect by operating at various temperature levels, such as $T_s$ and $T_l$ in FIG. 10. For example, in FIG. 10(a), the elongated curve represents the temperature evolution near the focal volume from the narrowband energy, while the pulse is representative of the ultrawideband radiation (electric field). The ultrawideband pulse is at time $T_S$. The synergistic effect is shown by the dashed curve.

Figure 10:
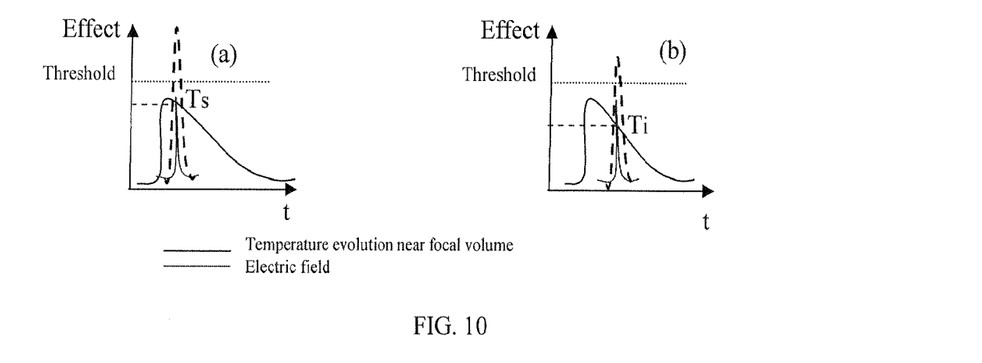
FIG. 10. Setting the delay time of ultrawideband pulses to the narrowband microwave allows determining the timing and consequently the intensity of the synergistic effect: (a). short delay, (b) increased delay.

Adding a delay to the ultrawideband pulse can affect the intensity of the synergistic effect. For example, referring to FIG. 10(b), the ultrawideband pulse can be performed at a later time, time $T_l$. As represented by the dashed curve in FIG. 10(b), the intensity of the synergistic effect can be reduced.

Figure 11:
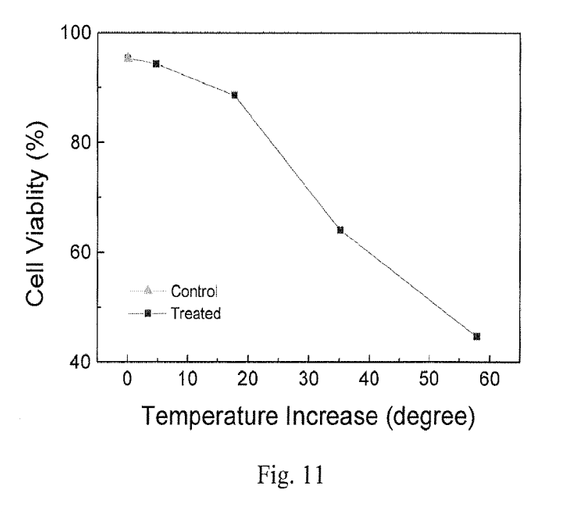
FIG. 11 illustrates a cell viability versus temperature increase graph.
Figure 12:
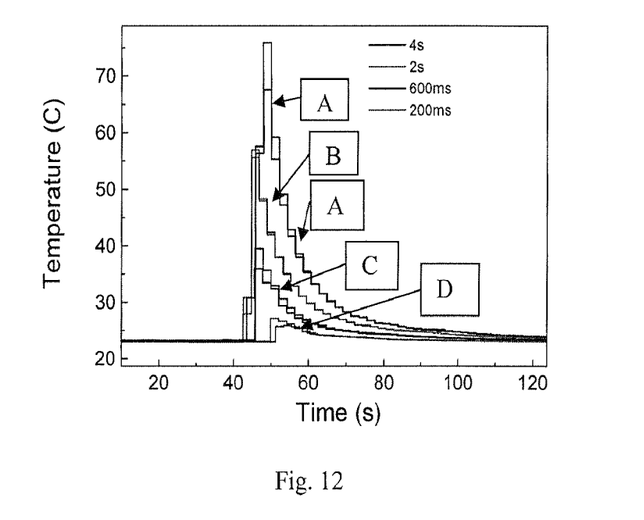
FIG. 12 shows a temperature increase versus pulse duration graph.

Some cells are rather sensitive to small changes in temperature, as shown in FIG. 11. This graph shows the results of measurements of the cell viability of liver cancer cells (Hep1/-6), versus temperature at a constant temperature rise. Starting at room temperature and up to a temperature increase of 5 C. for a pulse duration of 0.2 seconds, the effect on cells may be negligible. This means that the viability is essentially unchanged (100%). Above a temperature increase of 18 C., however, the viability decreases rapidly. In order to define the treated volume, the power deposition which determines the temperature in the focal volume would then need to be set to values such that the volume which needs to be spared, would be heated to less than the critical temperature. The temperature variation was achieved by increasing the pulse duration but still keeping the total pulse duration small compared to the diffusion time. The temporal temperature distribution for pulses with increasing duration is shown in FIG. 12. Here, the diffusion time in this particular medium is approximately twenty seconds. Distribution A represents the temperature increase for a pulse duration of four seconds; distribution B represents the temperature increase for a pulse duration of two seconds; distribution C represents the temperature increase for a pulse duration of 600 ms; and distribution D represents the temperature increase for a pulse duration of 200 ms. The treatment would therefore utilize high power radiowave or microwave generators, which will allow a well controlled increase in power, and consequently in temperature in the focal area. The temperature can be monitored with a wideband imaging system.

The subject matter described herein, including the steps of the methodologies described above, can be realized in hardware, software, or a combination of hardware and software. It can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The subject matter described herein, including the steps of the methodologies described above, can be embedded in a computer program product. The computer program product can comprise a computer-readable storage medium in which is embedded a computer program comprising computer-executable code for directing a computing device or computer-based system to perform the various procedures, processes and methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The foregoing description of embodiments has been presented for the purposes of illustration. The embodiments are not intended to limit the claimed subject matter to the precise forms disclosed. Indeed, modifications and variations will be readily apparent from the foregoing description.

We claim:

1. A method for inducing cell death in patient tissue, the method comprising:
    generating a first radiation and a second radiation;
    directing the first radiation and the second radiation to a focusing element; and
    directing the first radiation and the second radiation towards the patient tissue with at least one focusing element,
    wherein the first radiation comprises a plurality of pulses and is configured to elevate temperatures in at least a portion of the patient tissue including a target volume to cause a distribution of temperatures in the patient tissue
    wherein the second radiation produces a distribution of electric fields in the patient tissue configured to affect cell functions in the target volume non-thermally, and
    wherein the directing comprises adjusting the relative position of a peak of the distribution of temperatures and a peak of the distribution of electric fields so that a predetermined target combination of temperatures and electric fields is provided in the target volume.

2. The method of claim 1, wherein the first radiation is narrowband radiation in the microwave range.

3. The method of claim 1, wherein the first radiation is narrowband radiation, and wherein the frequency of the narrowband radiation is at least 100 MHz.

4. The method of claim 1, wherein the first radiation is narrowband radiation, and wherein the frequency of the narrowband radiation is less than 100 GHz.

5. The method of claim 1, wherein a power level of the first radiation exceeds approximately 100 watts.

6. The method of claim 1, wherein a power level of the first radiation is less than 1 megawatt.

7. The method of claim 1, wherein the second radiation is ultra-wideband radiation using at least one ultra-short electrical pulse.

8. The method of claim 7, wherein the at least one ultra-short electrical pulse has a rise time of less than one nanosecond.

9. The method of claim 7, wherein the at least one ultra-short electrical pulse has a pulse duration of more than 10 picoseconds.

10. The method of claim 7, wherein the at least one ultra-short electrical pulse has a pulse duration of less than 10 nanoseconds.

11. The method of claim 7, wherein the at least one ultra-short electrical pulse has a power level of at least one megawatt.

12. The method of claim 7, wherein the at least one ultra-short electrical pulse has a power level of less than one gigawatt.

13. The method of claim 1, wherein the focusing element comprises at least one prolate spheroidal reflector.

14. The method of claim 1, wherein the focusing element comprises at least one focusing lens.

15. The method of claim 1, wherein the second radiation is ultra-wideband radiation and the ultra-wideband radiation is at least one ultra-short electrical pulse.

16. The method of claim 15, wherein the at least one ultra-short electrical pulse has a rise time of less than one nanosecond.

17. The method of claim 1,
    subsequently treating the patient tissue with another mode of treatment.

18. The method of claim 17, wherein the other mode of treatment comprises ionizing radiation.

19. The method of claim 17, wherein the other mode of treatment comprises the local application of a chemotherapeutic agent.

20. The method of claim 17, wherein the other mode of treatment comprises the local application of drugs which lead to cell death.

21. The method of claim 17, wherein the other mode of treatment comprises ultrasound radiation.

22. The method of claim 17, wherein focusing comprises focusing the ultra-wideband radiation with at least one prolate spheroidal reflector.

23. The method of claim 17, wherein focusing comprises focusing the ultra-wideband radiation with at least one focusing lens.

24. The method of claim 17, wherein the ultra-wideband radiation is an ultra-short electrical pulse.

25. A system for locally inducing cell death in patient tissue, the system comprising:
- an antenna;
- a first power source configured for generating a first radiation;
- an first antenna coupled to the first power source for receiving the first radiation and comprising an first focusing element for directing the first radiation towards a target volume;
- a second power configured for generating a second radiation;
- a second antenna coupled to the second power source for receiving the second radiation and comprising a second focusing element for directing the second radiation towards the target volume; and
- a controller coupled to the first power source, the second power source, the first antenna, and the second antenna, wherein the controller is configured for:
    - controlling the first power source so as to configure the first radiation to comprise a plurality of pulses configured to elevate temperatures in at least a portion of the patient tissue situated in the target volume to cause a distribution of temperatures in the patient tissue, and
    - controlling the second power source so as to configure the second radiation to produce a distribution of electric fields in the patient tissue configured to affect cell functions in at least a portion of the patient tissue situated in the target volume non-thermally,
    - controlling the first antenna and the second antenna to adjust the relative position of a peak of the distribution of temperatures and a peak of the distribution of electric fields so that a pre-determined target combination of temperatures and electric fields is provided in the patient tissue situated in the target volume.

26. The system of claim 25, wherein the focusing element comprises a prolate spheroidal reflector or a lens.

27. The system of claim 25, wherein the first radiation is narrowband radiation, and wherein the second radiation is ultra-wideband radiation and the ultra-wideband radiation is at least one ultra-short electrical pulse.

* * * * *